(12) United States Patent
Kitagawa et al.

(10) Patent No.: US 6,408,047 B1
(45) Date of Patent: Jun. 18, 2002

(54) METHOD OF PROVIDING HIGH THROUGHPUT PROTEIN CRYSTALLOGRAPHY

(75) Inventors: Mel Kitagawa; Keith Crane; Paul N Swepston; Joseph D Ferrara, all of The Woodlands, TX (US)

(73) Assignee: Rigaku/MSC, Inc., The Woodlands, TX (US)

( * ) Notice: Subject to any disclaimer, the term of this patent is extended or adjusted under 35 U.S.C. 154(b) by 0 days.

(21) Appl. No.: 09/678,767

(22) Filed: Oct. 4, 2000

(51) Int. Cl.[7] .............................................. G01N 23/30
(52) U.S. Cl. ........................................... 378/79; 378/80
(58) Field of Search ..................... 378/79, 80; 414/737, 414/739, 741

(56) References Cited

U.S. PATENT DOCUMENTS 4,676,070 A * 6/1987 Linner ........................... 62/64
6,064,717 A     5/2000 Ortega et al.

FOREIGN PATENT DOCUMENTS

| JP | 09033453 A | * | 2/1997 | .......... G01N/23/20 |
| JP | 409033453 A | * | 2/1997 | .......... G01N/23/20 |
| WO | WO 01/11345 A2 | * | 2/2001 | .......... G01N/23/00 |

* cited by examiner

*Primary Examiner*—Robert H. Kim
*Assistant Examiner*—Irakli Kiknadze
(74) *Attorney, Agent, or Firm*—R. Perry McConnell

(57) ABSTRACT

The invention provides a method of performing x-ray crystallography on samples by using a robot to select the target sample, to position the sample for x-ray crystallography, and to deposit the sample, all without transferring the sample to another device, such as a goniometer. This method allows high throughput, automated crystallography, thereby providing a high volume of samples to be tested while lessening the need for human intervention.

6 Claims, 4 Drawing Sheets

METHOD OF PROVIDING HIGH THROUGHPUT PROTEIN CRYSTALLOGRAPHY

TECHNICAL FIELD

The invention concerns providing automated, high throughput protein crystallography.

BACKGROUND OF THE INVENTION

X-ray crystallography is typically performed by diffracting x-rays through a crystalline sample and determining the resultant pattern of diffracted radiation on a detector or target. Commercially available systems typically involve the use of a goniometer to which the sample is mounted. Goniometers provide accurate angular measurement and control needed for x-ray crystallography, but are also expensive. Further, commercially available goniometers do not provide for rapid and efficient robotic mounting or dismounting of samples. Although mechanisms to mechanically transfer samples to and from goniometer mounts are possible, such mechanisms are cumbersome. Moreover, combining such mechanisms with goniometers in an effort to achieve automation results in an inherently more complex, and therefore less reliable, mechanical system.

One alternative to a goniometer-based x-ray crystallography system is to use independently mounted x-ray source, sample holder, and detector, as described in U.S. Pat. No. 6,064,717 to Ortega, et al. Such a system allows for computer control of the source, holder, and detector positioning, and avoids the necessity of a goniometer-style mounting system.

However, new techniques in biochemistry and protein analysis will require an automated system for performing protein crystallography, so that large numbers of samples may be tested efficiently. Doing so effectively will require as simple a mechanical system as possible, to minimize potential breakdowns and reduce the need for human intervention. Thus, it is desirable to provide a robotic crystallography system which incorporates the use of multiply-independent x-ray source, sample, and detector, and which can also automatically select a sample from a group of samples to be tested, move the sample into position, test the sample, and deposit the sample for later use or disposal.

This procedure is complicated by the need in protein crystallography to regulate the sample temperature by keeping the samples at a controlled, usually reduced, temperature. Samples are generally stored in a temperature-regulated environment, such as a dewar containing liquid nitrogen, prior to and after testing. Further, each sample may be equipped with a portable liquid nitrogen bath which will protect the sample's temperature while it is being moved from the storage location to the testing location. Such a portable bath must be decoupled from the sample while the sample is being tested, and the sample must be maintained in a temperature controlled state during testing. After testing, it is necessary to recouple the portable nitrogen bath to the sample for transportation back to a protected environment, so that the sample will always be maintained in a temperature controlled state in case the sample is needed for further experimentation.

It is an object of this invention to provide a robotic x-ray crystallography system in which multiple samples may be automatically, selectively tested, and in which the sample selector also provides the function of a goniometer during testing.

It is a further object of this invention to provide such a robotic x-ray crystallography system in which a sample to be tested is coupled and subsequently uncoupled from a robotic selector arm only once during each testing cycle.

It is another object of this invention to protect samples from degradation by maintaining them in a temperature controlled state at all phases of the testing cycle.

BRIEF DISCLOSURE OF THE INVENTION

Samples used in crystallography, such as protein samples, must often be maintained in an artificial environment, for example, they may be maintained at a substantially reduced temperature. This description is directed, as an example, to maintaining temperature controlled samples at liquid nitrogen temperatures or other selected, reduced temperatures, although those of skill in the art will recognize that other means of controlling temperature are possible, and that such known variations in maintaining artificial environments are incorporated in the scope of this description.

For high-throughput x-ray crystallography, a set of samples will be provided and stored in a controlled environment, such as a first storage dewar containing liquid nitrogen. As those of skill in the art will recognize, many variations on such an arrangement are possible, and the samples can be arrayed in a fixed arrangement, on a conveyor system, or in any other such manner of positioning, or moving the samples into position, as shall be convenient to the purpose of placing the samples in a position where they may be selectively coupled to a robotic selector, and which allows the continuous identification of each sample.

Each sample may be connected to a sample holder, which comprises an extension or other point which may be selectively coupled onto by a robotic grasping device. This grasping point provides a fixed spatial relationship to the sample, so that positioning the sample holder by positioning the grasping point will also fix the spatial location of the sample. Additionally, each sample holder may comprise an integral or attachable collar (or similar connector) to allow the selective coupling and uncoupling of a liquid reservoir to the sample holder in such a fashion that the sample will be contained within the liquid reservoir when it is connected to the sample holder.

To perform high-throughput crystallography on the samples, a robotic arm with a coupling device capable of grasping an individual sample is operated under automatic control, such as by a program stored within the robotic device or on a separate, connected computer. The robotic arm is comprised of known components, such as base, support, wrist, elbow, and hand, in such combination as is necessary to provide the degree of articulation necessary to allow the robotic arm to perform its functions. The robotic hand comprises a grapple capable of securely gripping the grasping point of a sample holder. Once a sample is selected and gripped by the robotic arm, the arm is then moved to the necessary position to serve in the capacity of a goniometer, positioning the sample holder so that the sample will be placed in a known spatial relationship to an x-ray source and a detector.

Because the samples must be maintained at an artificial temperature, provision is also made for protecting the sample during the transition from the initial storage area to the testing area. In the example of using liquid nitrogen, each sample holder is provided with a collar or other mechanical element to which a liquid nitrogen reservoir may be selectively coupled and uncoupled. While in the first storage dewar, each sample is pre-coupled to a liquid reservoir, so that when the sample is lifted out of the first storage dewar, the liquid reservoir is carried with the sample to keep the sample immersed in liquid nitrogen while it is in transition.

Once the sample is in position for x-ray crystallography to be performed, a controlled temperature gas stream, for example, nitrogen or helium, is directed over the sample and the liquid reservoir. The gas is refrigerated sufficiently to insure that the sample will remain at a controlled temperature while within the controlled temperature gas stream. A second robotic tool may then be used to grasp and decouple the liquid reservoir from the sample holder and to remove the liquid reservoir from the region of the sample so that x-ray crystallography can be performed on the sample. Prior to or during the x-ray crystallography process, the robotic arm provides all necessary spatial adjustments to the sample position, and orients or rotates the sample as necessary.

As an alternative to using a liquid reservoir to maintain the sample in an artificial environment while it is being moved from or to a storage dewar such as the first storage dewar, the controlled temperature gas stream may be provided through a jet which is attached to the first robotic arm or otherwise designed to travel with the first robotic arm. In this alternative configuration, the controlled temperature gas stream may be directed over the sample from the time it leaves the first storage dewar until the time it is replaced in the first storage dewar or otherwise released from the first robotic arm. Using such a configuration, the fluid reservoir would not be required, nor would the second robotic tool be required to couple and uncouple the fluid reservoir from the sample holder.

Those of skill in the art will recognize that performing x-ray crystallography on the sample requires an x-ray source and a detector, and that many variations and combinations of these devices are possible and known in the art. For example, the x-ray source can be an x-ray tube, a rotating anode, or a synchrotron source and will include beam conditioning optics including collimation or slits. A suitable detector will be any device capable of measuring diffraction events, including imaging plate detectors, CCD detectors, multiwire detectors, and digital pixel array detectors.

After testing, the second robotic tool is used to replace the liquid reservoir and to recouple it to the sample holder, so that the sample may be removed from the controlled temperature gas stream and remain at a controlled temperature. The robotic arm can then place the sample in a receiver dewar in a manner that allows for its continued identification, or can return the sample to the first storage dewar and replace it therein. Whether the sample is returned to the original dewar or placed in a second dewar is not critical to the functioning of this invention, and will be recognized by those of skill in the art as variable arrangements made for the convenience of the system's users.

DESCRIPTION OF THE PREFERRED EMBODIMENT

Figure 1:
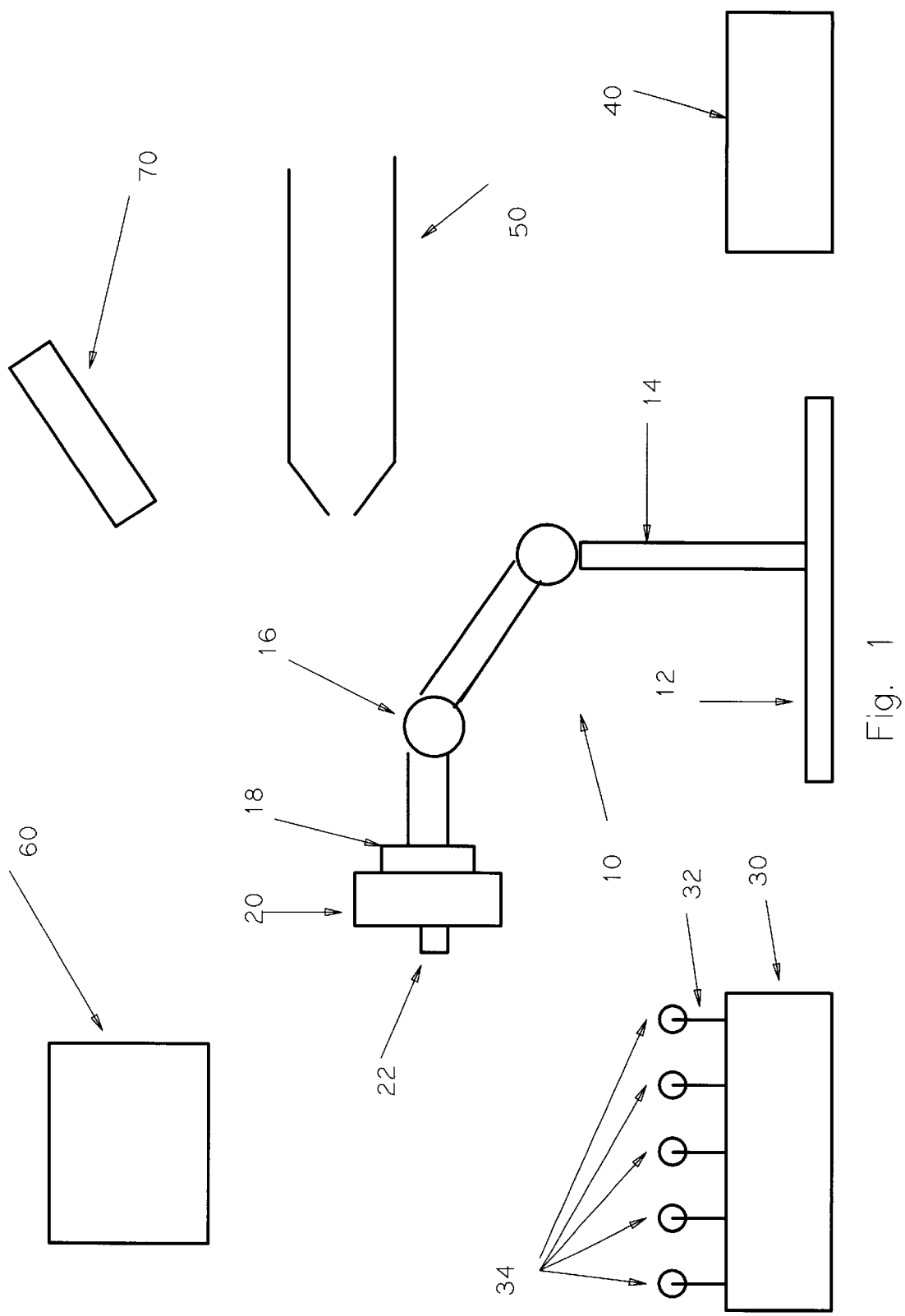
FIG. 1 is a schematic representation of the elements of a high throughput x-ray crystallography system.

Referring to FIG. 1, the robotic arm 10 comprises a combination of a base 12, support 14, elbow 16, wrist 18, and hand 20. Those of skill in the art will recognize that multiple combinations of these components are possible, and that the particular combination used will result from the engineering requirements of the particular implementation of the system. The hand 20 comprises a grapple 22, which is used to selectively hold the grasping point 34 of a sample holder 32.

The samples (not depicted in FIG. 1) are retained in an artificial environment. Where the desire is to keep the samples at a controlled low temperature, as in protein crystallography, the samples may be retained in a liquid nitrogen bath in a first storage dewar 30. The first storage dewar 30 may be of any known configuration, and will provide some means of ordering the samples, such as keeping the sample holders 32 in an ordered array, or by moving the sample holders 32 in a known sequence.

The other elements of the high throughput x-ray crystallography system include an x-ray radiation source 60, a two-dimensional detector 70, a controlled temperature gas stream jet 50, and an optional second storage dewar 40. The radiation source 60 may be an x-ray tube, a rotating anode, or a synchrotron source and will include beam conditioning optics including collimation or slits. A suitable detector 70 will be any device capable of measuring diffraction events in two dimensions, including imaging plate detectors, CCD detectors, multiwire detectors, and digital pixel array detectors. The radiation source 60, detector 70, and robotic arm 10 must be appropriately positioned during the actual performance of x-ray crystallography on a sample. As those of skill in the art will recognize, this positioning may be accomplished on a pre-determined basis with the selection of a suitable set of radiation source 60 and detector 70. In the preferred embodiment, the positions of the radiation source 60, detector 70, and robotic arm 10 will be dynamically controlled by a control device such as a computer (not shown), using the method of U.S. Pat. No. 66.064,717 to Ortega, et al.

The controlled temperature gas stream jet 50 is a device capable of directing a continual stream of refrigerated gas, such as refrigerated nitrogen, through the region in which the sample will be positioned during the performance of x-ray crystallography. The optional second storage dewar 40 can serve as a receptacle for tested samples, again with provisions to retain the samples in a controlled environment, such as a liquid nitrogen bath. Alternatively, the samples may be replaced in the first storage dewar 30 after x-ray crystallography has been performed.

Figure 2:
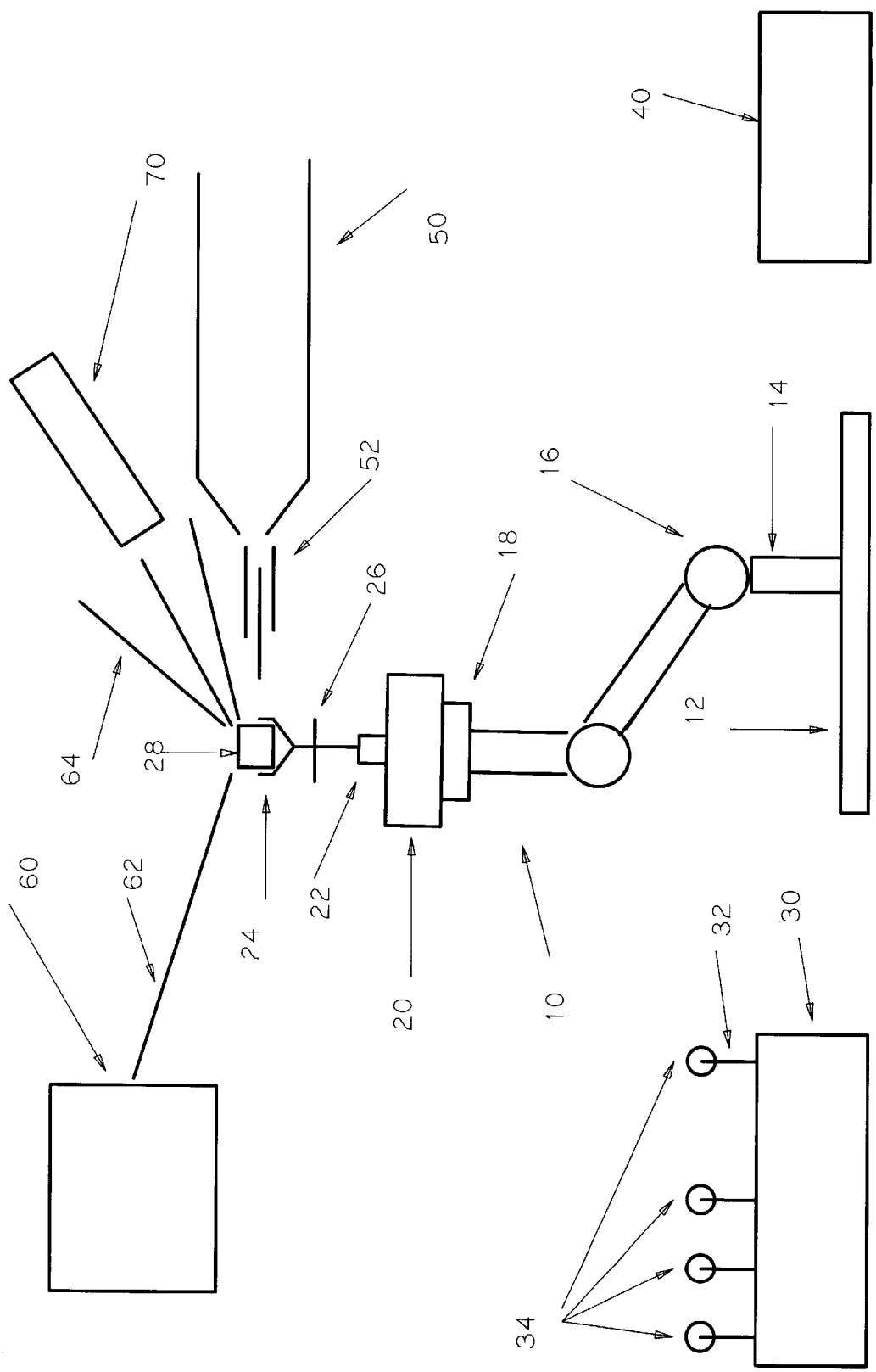
FIG. 2 is a schematic representation of the elements of a high throughput x-ray crystallography system during the performance of x-ray crystallography on a sample.

Referring to FIG. 2, a schematic representation of a sample undergoing x-ray crystallography is shown. A sample 28 is retained in its respective sample holder 24, which is in turned held in position by grapple 22 on the robotic arm 10. The robotic arm 10 has been maneuvered under automated control to select the sample holder 24 from among the sample holders 32 arrayed in the first storage dewar 30. Grapple 22 has gripped the appropriate grasping point 34, and the robotic arm 10 has moved the sample holder 24 so that sample 28 is positioned for x-ray crystallography.

Figure 3A:
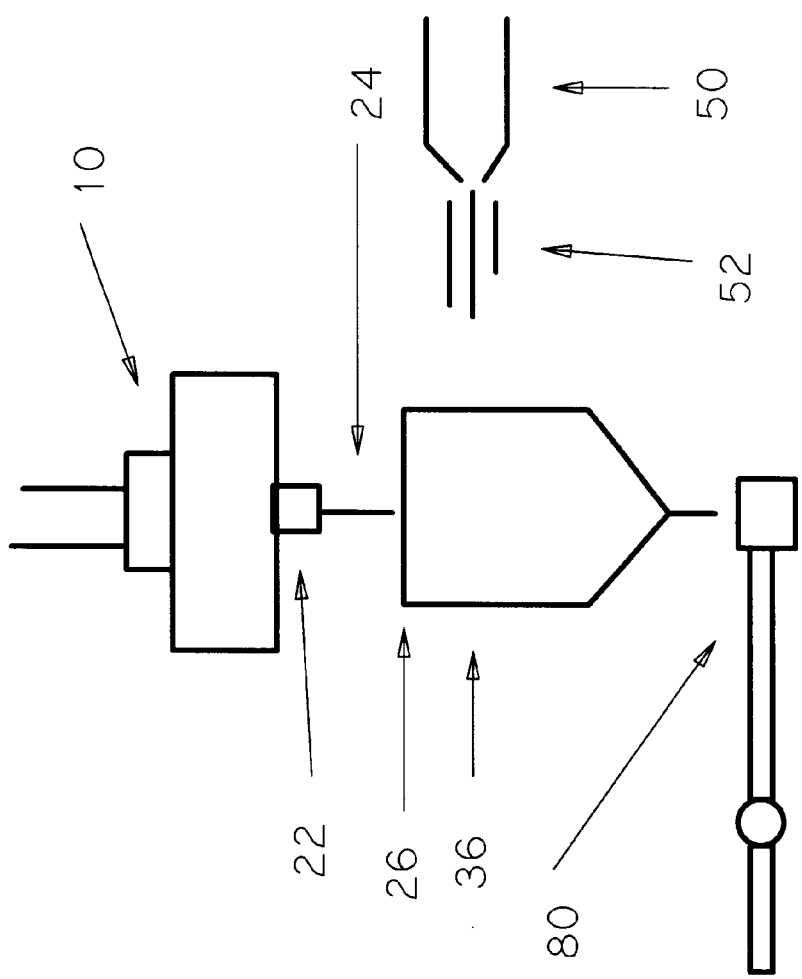
FIG. 3A is a schematic representation of one embodiment of the environmental control system.
Figure 3B:
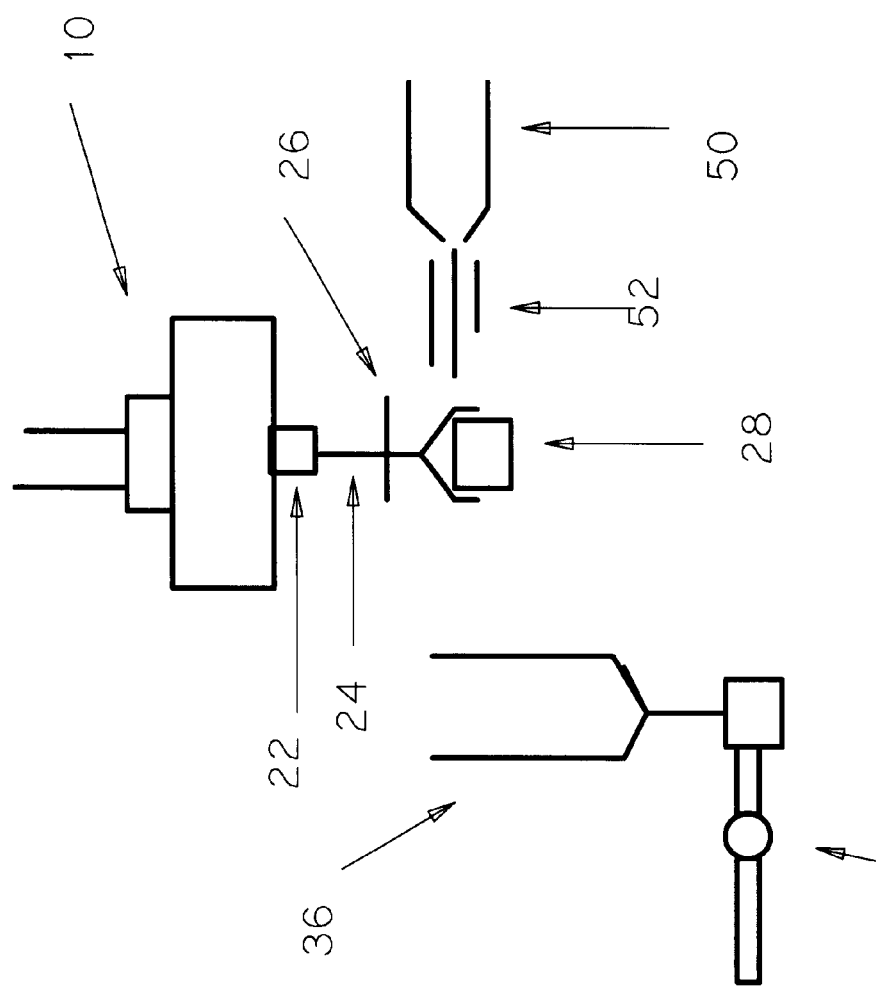
FIG. 3B is a schematic representation of an embodiment of the environmental control system with the sample in position for testing.

Referring to FIGS. 3A and 3B, an intermediate step in the movement of sample 28 is shown. While awaiting testing, samples are protected from undesirable temperature changes during the transition from the first storage dewar by being retained inside a fluid reservoir 36 which is coupled to the sample holder 24 by a collar 26. After the selected sample holder 24 is removed from the first storage dewar by robotic arm 10, it is positioned so that the sample 28 is in position for x-ray crystallography to be performed. A controlled temperature gas stream 52, such as a continual flow of refrigerated nitrogen, is directed by controlled temperature gas stream jet 50 over the fluid reservoir 36, so that once the fluid reservoir 36 is removed, the controlled temperature gas stream 52 will prevent sample 28 from undesirable temperature changes. A second robotic arm 80 is used to grasp the fluid reservoir 36, de-couple it from the collar 26, lower it from around the sample 28, and move it out of the zone needed for x-ray crystallography. Those of skill in the art will recognize that the design of the second robotic arm 80, the fluid reservoir 36, and the collar 26 may take any of a number of practical engineering forms. Thus, the term "collar" may refer to any of a number of coupling devices which will allow an appropriately shaped fluid reservoir to be coupled and uncoupled to a sample holder by robot control, and is intended to encompass all such devices. Similarly, the second robotic arm 80, may be fully independent of the first robotic arm 10, or it may be mechanically joined to the first robotic arm 10.

After x-ray crystallography is performed on the sample 28, and before the controlled temperature gas stream 52 is interrupted, the second robotic arm 80 may be used to reattach the fluid reservoir 36 to the collar 26, so that the sample may be preserved in a controlled temperature state for further use.

Referring again to FIG. 2, the robotic arm 10 functions as a goniometer, positioning the sample 28 appropriately for the performance of x-ray crystallography. So long as sample 28 remains positioned within controlled temperature gas stream 52, the robotic arm may be freely moved to spatially orient the sample 28 at any desired orientation, or to rotate the sample 28 as necessary. X-rays 62 from radiation source 60 are directed at the sample 28, and the resulting diffraction pattern 64 is determined by detector 70. By continuing to select, test, and release samples by using the robotic arm 10 as both a sample selector and goniometer, high-throughput x-ray crystallography may be performed on a large number of samples and wholly under automated control. In general, the number of samples which can be processed in any one group will be limited only by such factors as spatial limitations on the size of the first storage dewar 30 and the need to replenish the liquid nitrogen supplies.

We claim:

1. A method of performing crystallography, comprising using a robot to select a sample, using said robot to selectively position the sample, maintaining the sample in an artificial environment, and performing x-ray crystallography on the sample without decoupling the sample from said robot.

2. The method of claim 1, additionally comprising the step of using said robot to selectively release the sample after crystallography is completed.

3. The method of claim 1, additionally comprising the steps of providing an environmental container for storing the sample in an artificial environment, and selectively removing the sample from said environmental container before said step of performing x-ray crystallography.

4. The method of claim 3, additionally comprising the step of selectively replacing the sample into said environmental container after said step of performing x-ray crystallography.

5. The method of claim 1, wherein said step of maintaining the sample in an artificial environment comprises the steps of selectively directing a stream of gas over the sample, and controlling the temperature of said stream of gas to regulate the temperature of the sample.

6. The method of claim 2, additionally comprising the step of using said robot to selectively re-position the sample prior to the step of selectively releasing the sample.

* * * * *